(12) United States Patent
Lin et al.

(10) Patent No.: US 6,712,770 B2
(45) Date of Patent: Mar. 30, 2004

(54) BREATH-BASED DIAGNOSTIC DEVICE INCLUDING AN ARRAY OF MULTIPLE SENSORS

(75) Inventors: Yuh-Jiuan Lin, Taipei (TW); Hong-Ru Guo, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 51 days.

(21) Appl. No.: 10/154,365

(22) Filed: May 23, 2002

(65) Prior Publication Data

US 2003/0060726 A1 Mar. 27, 2003

(30) Foreign Application Priority Data

May 23, 2001 (TW) ........................................ 90112368 A

(51) Int. Cl.⁷ .................................................. A61B 5/08
(52) U.S. Cl. ........................ 600/532; 600/529; 600/543
(58) Field of Search ................................ 600/529, 531, 600/532; 73/23.3

(56) References Cited

U.S. PATENT DOCUMENTS

| | | | | |
|---|---|---|---|---|
| 6,234,006 B1 | * | 5/2001 | Sunshine et al. | 73/29.01 |
| 6,248,078 B1 | * | 6/2001 | Risby et al. | 600/529 |
| 6,461,306 B1 | * | 10/2002 | Hanson et al. | 600/532 |
| 6,467,333 B2 | * | 10/2002 | Lewis et al. | 73/31.05 |
| 6,468,222 B1 | * | 10/2002 | Mault et al. | 600/531 |

* cited by examiner

*Primary Examiner*—Robert L. Nasser
*Assistant Examiner*—Patricia Mallari
(74) *Attorney, Agent, or Firm*—Merchant & Gould P.C.

(57) ABSTRACT

A breath-based diagnostic device. The device includes an array of multiple gas sensors, a database storage device and a microprocessor. The gas sensors contain material capable of reacting with volatile organic chemicals in the exhaled breath of the subject. The database storage device stores established responses to a variety of disease. The microprocessor compares the response detected by the gas sensors and the database so as to perform the diagnosis.

19 Claims, 4 Drawing Sheets

FIG. 3

| PATTERN ANALYSIS | PROBE SERIAL NO.:1.6 | 01-14-1999 |
|---|---|---|
| ANALYTE:<br>tma | TMA 5.86mg/l | |
| AMPLITUDE:<br>cytC:.6063917<br>pb2:.3548193<br>pb22:.2168119<br>A7  :2.34275<br>A8  :2.919847<br>A1  :1.268506<br>Scale Factor:<br>1:34 | | |
| FILE:6T2081.smd | | CONC.0 |

| PATTERN ANALYSIS | PROBE SERIAL NO.:1.6 | 01-14-1999 |
|---|---|---|
| ANALYTE:<br>mma | MMA 4.47mg/l | |
| AMPLITUDE:<br>cytC:.5345534<br>pb2:.3584337<br>pb22:.1363403<br>A7  :1.725047<br>A8  :.9223918<br>A1  :.5800807<br>Scale Factor:<br>1:34 | | |
| FILE:6M12041.smd | | CONC.0 |

| PATTERN ANALYSIS | PROBE SERIAL NO.:1.6 | 01-14-1999 |
|---|---|---|
| ANALYTE:<br>tma | DMA 3.78mg/l | |
| AMPLITUDE:<br>cytC:.0917782<br>pb2:5.843373E-02<br>pb22:2.357765E-02<br>A7  :.1175869<br>A8  :.475827<br>A1  :.5380794<br>Scale Factor:<br>1:34 | | |
| FILE:6D1208.smd | | CONC.0 |

| PATTERN ANALYSIS | PROBE SERIAL NO.:1.6 | 01-14-1999 |
|---|---|---|
| ANALYTE:<br>formic acid | Formic acid 1.33mg/l | |
| AMPLITUDE:<br>cytC:.0917782<br>pb2:5.843373E-02<br>pb22:2.357765E-02<br>A7  :.1175869<br>A8  :.475827<br>A1  :.5380794<br>Scale Factor:<br>1:34 | | |
| FILE:6F1205.smd | | CONC.0 |

| PATTERN ANALYSIS | PROBE SERIAL NO.:1.6 | 01-14-1999 |
|---|---|---|
| ANALYTE:<br>nh3 | NH$_3$ 4.86mg/l | |
| AMPLITUDE:<br>cytC:.2619503<br>pb2:.2078313<br>pb22:.3018965<br>A7  :1.559322<br>A8  :2.128499<br>A1  :1.963661<br>Scale Factor:<br>1:34 | | |
| FILE:6N1205.smd | | CONC.0 |

| PATTERN ANALYSIS | PROBE SERIAL NO.:1.6 | 01-14-1999 |
|---|---|---|
| ANALYTE:<br>acetone | Acetone 7.21mg/l | |
| AMPLITUDE:<br>cytC:2.758809E-02<br>pb2:.0186747<br>pb22:1.845208E-02<br>A7  :-5.084746E-02<br>A8  :-4.961832E-02<br>A1  :-3.364738E-02<br>Scale Factor:<br>1:34 | | |
| FILE:6A1208.smd | | CONC.0 |

BREATH-BASED DIAGNOSTIC DEVICE INCLUDING AN ARRAY OF MULTIPLE SENSORS

BACKGROUND OF THE INVENTION

1. Field of the Invention

The present invention relates to a breath-based diagnostic device. In particular, the present invention relates to a breath-based diagnostic device including a array of multiple sensors. The present invention also relates to a breath-based diagnostic method.

2. Description of the Related Art

Many disorders are accompanied with elevated volatile organic chemical (VOC) levels in the patent's breath due to abnormal metabolism. Diagnosis of such disorders can therefore be achieved by breath test. However, disorder-related VOC presents in very low concentration in the breath and therefore requires high sensitivity to detect. Disorder-related VOC often contains more than one chemical and results from breath test are often complex, requiring extensive analysis. Gas chromatography—mass spectrometer analysis has been used in breath test diagnosis. For example, U.S. Pat. Nos. 5,996,586 and 6,180,414 disclose such method for diagnosis. However, gas chromatography—mass spectrometer analysis requires a large amount of breath to be concentrated into a suitable sample. Also, the data collected from a gas chromatography—mass spectrometer needs to be compared with a spectrum to obtain a useful result.

SUMMARY OF THE INVENTION

The object of the present invention is to solve the previously mentioned problems when using the gas chromatography—mass spectrometer method, and therefore provide a device enabling diagnosis of disorder or physiological state directly from breath. The present invention also provides a diagnostic method using the device. The diagnostic device of the present invention is non-invasive and quick. The operation of the diagnostic device is easy and thus no complex training is required. Moreover, with the diagnostic device of the present invention, sample concentration and heating process are avoided and multiple chemicals can be analyzed at the same time.

The diagnostic device of the present invention utilizes a multi-sensor array to detect specific volatile organic chemicals (VOC) in the breath. The multi-sensor array carries a substance that is reactive to the VOC as a sensory receptor. The data collected is compared with a database for a variety of disorders to diagnose disorders or physiological state. The database is built up by statistically analyzed data for the disorders.

Accordingly, the diagnostic device of the present invention comprises a multi-sensor array, a database storage device and a microprocessor. The multi-sensor array comprises a plurality of sensory devices, each reacting with specific VOC in breath to generate a signal. Each of the sensory devices reacts with the VOC directly or through a sensory receptor coating on the sensory device. The database contains information for a variety of disorders in the form of a pattern and/or digital record. The microprocessor receives the signal generated by the multi-sensor array and compares the signal with information stored in the database to give a result.

Another aspect of the present invention is a diagnostic method for disorder diagnosis. The method comprises the following steps. Breath to be tested is collected and allowed to react with a multi-sensor array. A signal is generated from the reaction and sent to a microprocessor. The signal is then compared with information in a database to determine the physiological state of the person. The multi-sensor array comprises a plurality of sensory devices each reacting with specific VOC in breath to generate a signal. Each of the sensory devices reacts with the VOC directly or through a receptor coating on the sensory device. The database contains information for a variety of disorders in the form of a pattern and/or digital record. The microprocessor receives the signal generated by the multi-sensor array and compares the signal with information stored in the database to give a diagnosis result.

According to the features of the present invention, the sensory device of the multi-array is a quartz crystal sensory device, a metal oxide semiconductor (MOS) sensory device, a surface acoustic wave (SAW) device, an electrode device, or a fiber optic device. MOS sensory device and electrode device are capable of reacting with specific VOC themselves. On the other hand, quartz crystal sensory device, SAW, and fiber optic devices need to be coated with an additional sensory receptor that reacts with specific VOC in the breath. Quartz crystal sensory device can be, for example, a piezoelectric quartz crystal sensory device.

According to another feature of the present invention, the sensory receptor is a conductive macromolecule, organic compound, organelle, peptide, protein, antibody, nucleic acid, metal oxide or metal.

According to another feature of the present invention, the signal generated from the multi-array is a pattern signal or a digital signal. The pattern, for example, can be a fingerprint, block chart, wave chart, or radio diagram.

According to another feature of the present invention, the diagnostic device is suitable for the diagnosis of disorders such as uremia, cirrhosis, hyper methionine disorder, ketoacidosis, diabetes, periodontosis, gingivitis, lung cancer, pulmonary abscess, schizophrenia, and intestinal obstruction.

According to another feature of the present invention, the diagnostic device of the present invention is suitable for the diagnosis of disorders relating to abnormal metabolism or microorganism infectious disease.

According to another aspect of the present invention, the method for disorder diagnosis of the present invention is suitable for the diagnosis of disorders such as uremia, cirrhosis, hyper methionine disorder, ketoacidosis, diabetes, periodontosis, gingivitis, lung cancer, pulmonary abscess, schizophrenia, and intestinal obstruction.

According to another aspect of the present invention, the method for disorder diagnosis of the present invention is suitable for the diagnosis of disorders relating to abnormal metabolism or microorganism-based infectious disease.

BRIEF DESCRIPTION OF THE DRAWINGS

Without intending to limit it in any manner, the present invention can be more fully understood by reading the subsequent examples and references made to the accompanying drawings, wherein:

FIG. 3 is a figure for normalized amplitude patterns of a variety of VOC generated using a piezoelectric quartz crystal multi-sensor array device according to an embodiment of the present invention;

DETAILED DESCRIPTION OF THE PREFERRED EMBODIMENT

Figure 1:
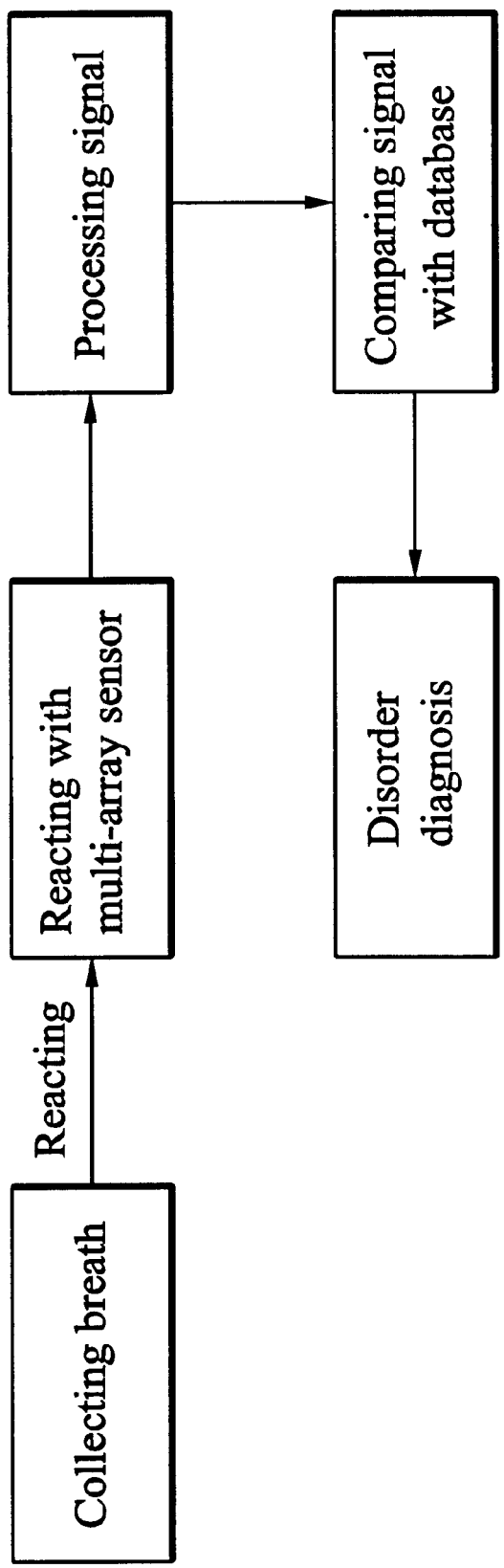
FIG. 1 is a flow chart of disorder diagnosis according to the present invention.

Please refer to FIG. 1, which is a flow chart of disorder diagnosis according to the present invention. The process comprises the following steps. Breath to be tested is collected and allowed to react with a multi-sensor array. A signal is generated from the reaction and sent to a microprocessor. The signal is then compared with information in a database using identifying software to diagnose the physiological state of the person.

Figure 2:
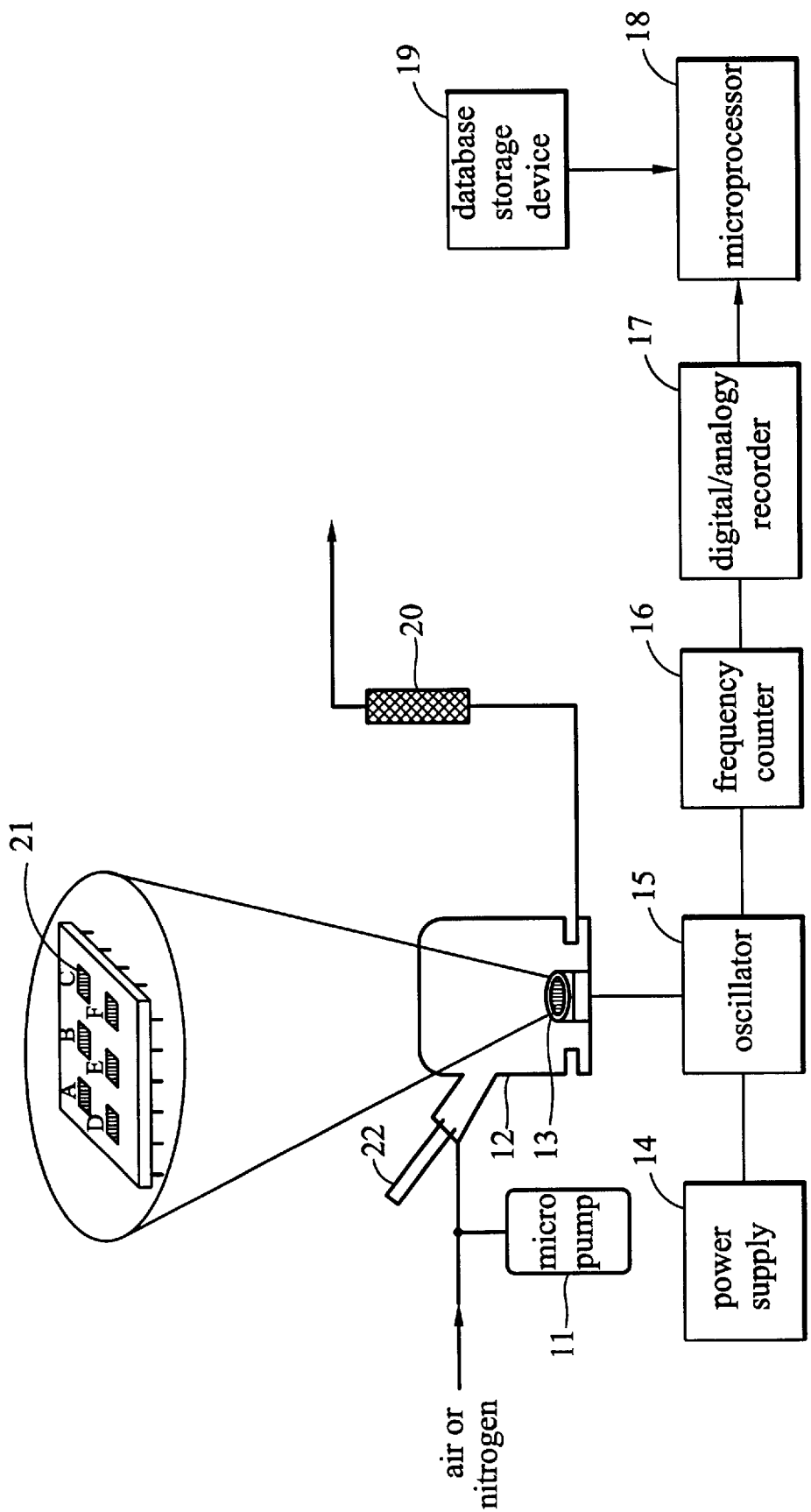
FIG. 2 is a structural diagram of a diagnostic device of an embodiment of the present invention.

Please refer to FIG. 2, which is a structural diagram of a diagnostic device of an embodiment of the present invention. The diagnostic device of the present invention comprises a sensory chamber 12; a signal processing unit comprising an oscillator 15, a frequency counter 16 and a digital/analog recorder 17; a microprocessor 18; database storage device 19. A multi-sensor array 13 composed of 6 piezoelectric quartz crystal 21 (the sensory device) is established in sensory chamber 12. When the breath to be tested is collected by a breath collecting device 22 and injected into sensory chamber 12, specific VOC in the breath reacts with the sensory receptor coated on the piezoelectric quartz crystal 21. An oscillation signal is generated from the reaction. The oscillation signal is then transmitted to oscillator 15 coupled to a power supply 14, counted in frequency counter 16, and transmitted to analog recorder 17 to generate a digital data. A plurality of records is stored in the database storage device 19. The digital data from digital/analog recorder 17 is received by microprocessor 18 and compared with the records from database storage device 19 to give out result of the diagnosis. Sensory chamber 12 is cleaned by nitrogen or air injected by a micro-pump 11 before the breath to be tested enters the breath collecting device. A flow meter 20 is also set up for observing flow of the breath, air, or nitrogen.

EXAMPLE 1

The piezoelectric quartz crystal multi-sensor array device as shown in FIG. 2 is used in this example. The piezoelectric quartz crystal multi-sensor array device used in this example has 6 AT-cut piezoelectric quartz crystal arrayed on a ceramic surface. Its oscillation frequency is 12 MHz. The surface of each piezoelectric quartz crystal is covered with gold foil as the electrode.

The piezoelectric quartz crystals of this example are also coated with a synthetic peptide as the sensory receptor. The synthetic peptide is produced based on the simulation of the affinity and energy of the binding between the disorder indicating VOC molecule and peptide. The peptide is then synthesized and used as the sensory receptor of the device of this example. Five such peptides, A7, A8, A1, pb2, pb22 and cytc (cytochrome C) are coated on the 6 piezoelectric quartz crystals of the piezoelectric quartz crystal multi-sensor array.

The disorder of interest in this example is uremia. The breath of uremia patient contains higher levels of trimethylamine (TMA), dimethylamine (DMA), monomethylamine (MMA), and ammonia ($NH_3$). These chemicals were chosen as the disease markers for the experiment. Breath samples of normal subjects, uremia patients, chronic kidney deficiency/chronic kidney failure patients were collected and analyzed with the multi-sensor array and accompanying software.

Reagent grade trimethylamine (45%, Sigma), dimethylamine (40%, Sigma), monomethylamine (40%, Sigma), ammonia (28%, Sigma), acetone (99.7% ALPS), and formic acid (90%, Kanto Chemical, Japan) were separately dissolved in volatile organic solvent. The solution was sealed in containers allowing the space above the solution to reach the saturate vapor pressure. The vapor of the head-space was analyzed with the diagnostic device of the present invention. The sensory chamber of the diagnostic device was cleaned with nitrogen prior to the testing. When the oscillation is stable, the volatile vapor of the chemicals was injected into the sensory chamber, and the resulting change in oscillation was measured and recorded. The resulting radar diagram is shown in FIG. 3. FIG. 3 shows the normalized amplitude patterns when the volatile vapor of trimethylamine, dimethylamine, monomethylamine, ammonia, acetone, and formic acid is introduced to the piezoelectric quartz crystal multi-sensor array device separately. Six piezoelectric quartz crystals coated with A7, A8, A1, pb2, pb22 and cytc respectively are represented as peaks with different orientations. As shown in FIG. 3, trimethylamine and ammonia have similar patterns, and dimethylamine and monomethylamine have similar patterns. On the other hand, formic acid and acetone have different patterns and the signal is very small. Therefore it is concluded that the diagnostic device of the present invention responds specifically and senstively to trimethylamine, dimethylamine, monomethylamine, and ammonia.

Figure 4:
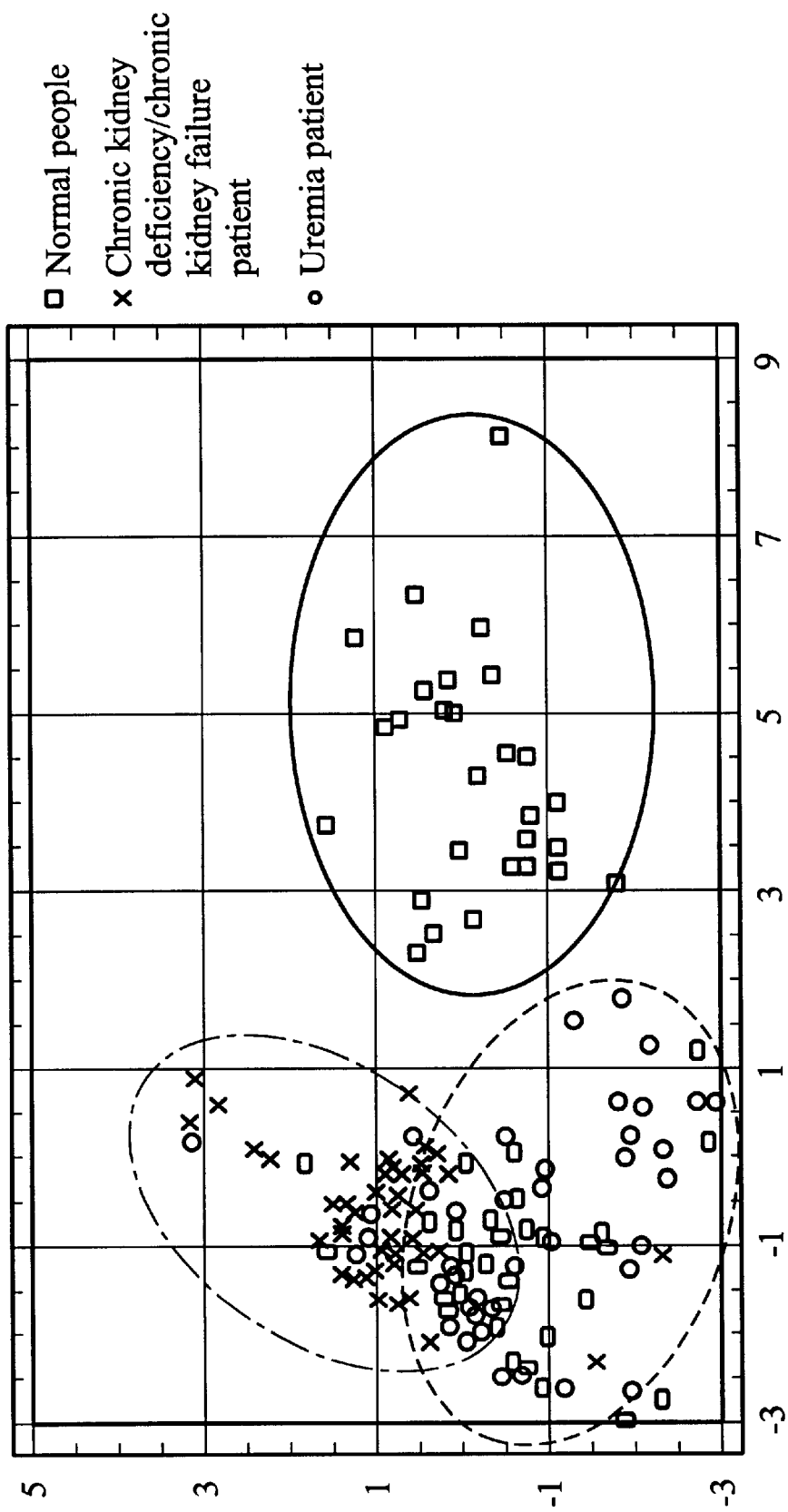
FIG. 4 is an analysis chart of breath test of normal subjects (□), uremia patients (○), and chronic kidney deficiency/chronic kidney failure patients (X).

Breath samples of normal subjects, uremia patients, chronic kidney deficiency/chronic kidney failure (CRI/CRF) patients were collected. These samples were collected from China Medical College Hospital (Taichung, Taiwan). The uremia patents had an average age of 51.6 (83 patients, age 29–80); chronic kidney deficiency/chronic kidney failure patients had an average age of 65 (61 patients, age 45–83); normal subjects had an average age of 32.8 (30 people, age 26–50). A 10 ml breath sample was used for the test. The resulting data was analyzed using the computer software "STATGRAPHICS plus" (Manugistics Inc.). The result is shown in FIG. 4. The differential analysis function index is shown in Table 1:

TABLE 1

| Sensor | Normal | CRI/CRF | Uremia |
| --- | --- | --- | --- |
| Sensor 1 | −0.056237 | 0.0971607 | 0.22747 |
| Sensor 2 | 0.289505 | 0.451251 | 0.31639 |
| Sensor 3 | 0.137522 | 0.107306 | −0.0523827 |
| Sensor 4 | 0.593452 | −0.00822516 | −0.0682361 |
| Sensor 5 | 0.0287422 | −0.0403459 | −0.123328 |
| Sensor 6 | 0.118828 | 0.0437494 | 0.0967424 |
| Constant | −20.4472 | −9.63871 | −12.1194 |

Sample differential results are shown in Table 2:

TABLE 2

| | | Differentiation rate | | |
| --- | --- | --- | --- | --- |
| | Sample | Normal | CRI/CRF | Uremia |
| Normal | 30 | 30 (100%) | 0 | 0 |
| CRI/CRF | 61 | 0 | 55 (90.16%) | 6 |
| Uremia | 33 | 1 | 16 | 66 (79.52%) |

From FIG. 4, Table 1 and Table 2, it is clear that the total differentiation rate of the samples (including normal subjects, chronic kidney deficiency/chronic kidney failure (CRI/CRF) patients, and uremia patients) was 86.78%. The differentiation rate for CRI/CRF patients was 90.16%. The differentiation rate for uremia patients was 79.52%. The differentiation rate for normal subjects was 100%.

Accordingly, the diagnostic device and diagnostic method of the present invention is proved to have high credit in the diagnosis of chronic kidney deficiency/chronic kidney failure and uremia.

EXAMPLE 2

Six peptides with high specificity and high sensitivity to the breath of cirrhosis patients were defined using a computer simulation program. The peptides, as the receptors, were separately coated on 12 MHz piezoelectric quartz crystal transducers of the sensory device according to the present invention.

Synthesis of the Peptide

Tertiary structure of olfactory protein was used as a template in the computer program "Insight II" to simulate possible binding sites for amine compounds. The selected peptide sequences were then modified according to properties of different amino acids to obtain peptide sequences that are both specific and sensitive to the cirrhosis breath. The peptides used in this example were synthesized by solid phase synthesis using Wang resin as the resin and F-moc as the protecting group in a Peptide Synthesizer (Apply Biosystems, 432A Peptide Synthesizer, USA).

Modification of the Peptide and Coating the Peptide on the Piezoelectric Quartz Crystal Each of the peptides was sulfurized using Traut's reagent. The peptide was then dissolved and diluted in a suitable organic solvent. The diagnostic device used in this example had a 12 MHz piezoelectric quartz crystal with a gold electrode. The gold electrode was incubated in 2–4 □l of the peptide solution at 45° C. overnight. The peptide was attached to the electrode through the sulfur atom, which forms a very steady covalent bond with the gold molecule of the electrode. The diagnostic device was ready for use when the detected frequency decrement was between 15000 and 20000 Hz. The procedure of coating the peptide to the diagnostic device was adjusted according to different properties of the peptide.

Preparation of Volatile Organic Vapor

Reagent grade dimethylamine, ammonia, acetone, butyric acid, and formaldehyde were separately dissolved in 5 ml of volatile organic solvent. The solution was sealed in separate 120 ml containers for 5 days allowing the space above the solution to reach the saturate vapor pressure. The concentration of the saturate vapor was calculated from the concentration of the solution and the saturate vapor pressure. The saturate vapor was used for the analysis with or without dilution.

Testing the Peptide with the Volatile Organic Vapor

The diagnostic device was tested with volatile vapor of dimethylamine, ammonia, acetone, butyric acid, and formaldehyde prepared as previously described and the results were analyzed by an analysis system (Smart Biotechnology Co., Ltd., Taipei, Taiwan). The volatile vapor used in the test was about 5 mg/l per test. The specificity and sensitivity of the peptides toward each of the previously mentioned volatile vapor were analyzed, and six peptides with the highest specificity and sensitivity were selected. These peptides were LC661, LC66, LC1311, LC48, LC79, and LC131.

According to Sauerbrey equation (Sauerbrey, 1959), frequency decrement of a piezoelectric quartz crystal is proportional to the mass applied to the piezoelectric quartz crystal. Therefore the coating quantity of peptide is indicated by the frequency decrement (Hz) after the peptide is coated on the piezoelectric quartz crystal. The coating quantities of the six selected peptides are listed in Table 3:

TABLE 3

|  | LC661 | LC66 | LC1311 | LC48 | LC79 | LC131 |
| --- | --- | --- | --- | --- | --- | --- |
| Peptide coating amount (Hz) | 6442 | 731 | 4890 | 8750 | 883 | 1148 |

The result of the volatile organic vapor (VOC) test is shown in Table 4:

TABLE 4

| | Peptides | | | | | |
| --- | --- | --- | --- | --- | --- | --- |
| VOC (5 mg/l) | LC661 | LC66 | LC1311 | LC48 | LC79 | LC131 |
| Dimethylsufide | 0.001087 | 0.012312 | 0.001022 | 0.000914 | 0.005663 | 0.002613 |
| Dimethyl-sulfide:H2O = 1:1 | 0.007141 | 0.023256 | 0.013292 | 0.004457 | 0.020385 | 0.004355 |
| Ammonia | 0.046725 | 0.143639 | 0.091411 | 0.043543 | 0.087203 | 0.051394 |
| Acetone | 0.001708 | 0.009576 | 0.002658 | 0.001029 | 0.005663 | 0.004355 |
| Butyric acid | 0.000776 | 0.009576 | 0.001022 | 0.000343 | 0.005663 | 0.002613 |
| Formaldehyde | 0.001087 | −0.00958 | −0.00143 | −0.00069 | −0.00566 | 0.002613 |

Sensitivity = □F/□m
□F = frequency decrease (Hz) after response with gas
□m = frequency decrease (Hz) after coating the receptor membrane on the crystal Breath Testing Breath samples of 31 normal subjects and 63 cirrhosis patients were collected at China Medical College Hospital (Taichung, Taiwan). The samples were tested with the six selected peptides using the diagnostic device of the present invention. The resulting data was analyzed using the computer software "STATGRAPHICS plus" (Manugistics Inc.). The result is shown in Table 5:

TABLE 5

| | | Predicted | |
| --- | --- | --- | --- |
| Actual | Group size | Cirrhosis | Normal |
| Cirrhosis | 63 | 60 (95.24%) | 3 (4.76%) |
| Normal | 31 | 3 (9.68%) | 28 (90.32%) |

Accordingly, the diagnostic device and diagnostic method of the present invention was proven to have high efficacy in the diagnosis of cirrhosis.

Finally, while the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A breath-based diagnostic device comprising:
   (a) a multi-sensor array comprising a plurality of sensory devices each reacting with specific volatile organic vapor in breath to generate a signal, wherein each of the sensory devices reacts with the volatile organic vapor directly and/or through a sensory receptor coated on the sensory device;
   (b) a database storage device for information storage;
   (c) a signal processing unit comprising a oscillator coupled to each of the sensory devices, a frequency counter coupled to the oscillator for counting oscillation frequency, and a digital/analog recorder for recording digital/analog data; and
   (d) a microprocessor for receiving a signal generated by the multi-sensor array and comparing the signal with information stored in the database.

2. The diagnostic device as set forth in claim 1, further comprising a breath collecting device.

3. The diagnostic device as set forth in claim 1, further comprising a display unit for displaying the information in the database and the comparison result generated by the microprocessor.

4. The diagnostic device as set forth in claim 1, wherein the multiple-array sensor is a quartz crystal sensor.

5. The diagnostic device as set forth in claim 4, wherein the quartz crystal sensor is a piezoelectric quartz crystal sensor.

6. The diagnostic device as set forth in claim 1, wherein the multiple-array sensor is a metal oxide semiconductor sensor.

7. The diagnostic device as set forth in claim 1, wherein the multiple-array sensor is a surface acoustic wave device.

8. The diagnostic device as set forth in claim 1, wherein the multiple-array sensor is an electrode device.

9. The diagnostic device as set forth in claim 1, wherein the multiple-array sensor is a fiber optic device.

10. The diagnostic device as set forth in claim 1, wherein the sensory receptor is a conductive polymer, organic compound, organelle, peptide, protein, antibody, nucleic acid, metal oxide or metal.

11. The diagnostic device as set forth in claim 1, wherein the signal generated from the multi-array is a pattern signal.

12. The diagnostic device as set forth in claim 11, wherein the pattern signal is a fingerprint, block chart, wave chart, or radio diagram.

13. The diagnostic device as set forth in claim 1, wherein the signal generated from the multi-array is a digital signal.

14. The diagnostic device as set forth in claim 1, wherein the diagnostic device is used for the diagnosis of uremia, cirrhosis, hyper methionine disorder, ketoacidosis, diabetes, periodontosis, gingivitis, lung cancer, pulmonary abscess, schizophrenia, or intestinal obstruction.

15. The diagnostic device as set forth in claim 1, wherein the diagnostic device is used for the diagnosis of disorders relating to abnormal metabolism.

16. A breath-based method for disorder diagnosis, comprising the following steps:
   collecting a breath sample from a subject to be diagnosed;
   reacting the breath sample with a breath-based diagnostic device comprising:
      (a) a multi-sensor array comprising a plurality of sensory devices each reacting with specific volatile organic vapor in breath to generate a signal, wherein each of the sensory devices reacts with the volatile organic vapor directly and/or through a sensory receptor coated on the sensory device;
      (b) a database storage device for information storage;
      (c) a signal processing unit comprising a oscillator coupled to each of the sensory devices, a frequency counter coupled to the oscillator for counting oscillation frequency, and a digital/analog recorder for recording digital/analog data; and
      (d) a microprocessor for receiving a signal generated by the multi-sensor array and comparing the signal with information stored in the database to generate a signal;
   comparing the signal with information in the database to determine the physiological state of the subject.

17. The breath-based method as set forth in claim 16, wherein the database comprises information for a variety of disorders in the form of a pattern and/or digital record.

18. The breath-based method as set forth in claim 16, wherein the method is used for the diagnosis of uremia, cirrhosis, hyper methionine disorder, ketoacidosis, diabetes, periodontosis, gingivitis, lung cancer, pulmonary abscess, schizophrenia, or intestinal obstruction.

19. The breath-based method as set forth in claim 18, wherein the method is used for the diagnosis of uremia or cirrhosis.

* * * * *